United States Patent
Barry et al.

(10) Patent No.: US 10,877,032 B2
(45) Date of Patent: *Dec. 29, 2020

(54) METHOD AND SYSTEM OF MICROFLUIDIC IMMUNOASSAY USING MAGNETIC BEADS

(71) Applicant: CALIPER LIFE SCIENCES, INC., Hopkinton, MA (US)

(72) Inventors: Andrew Barry, Chelmsford, MA (US); Laurel Provencher, Hopkinton, MA (US); Seth Cohen, Westford, MA (US); I-Jane Chen, Alameda, CA (US); Jun Yan, Franklin, MA (US); Jingjing Wang, Framingham, MA (US)

(73) Assignee: Caliper Life Sciences, Inc., Hopkinton, MA (US)

( * ) Notice: Subject to any disclaimer, the term of this patent is extended or adjusted under 35 U.S.C. 154(b) by 242 days.

This patent is subject to a terminal disclaimer.

(21) Appl. No.: 15/830,777

(22) Filed: Dec. 4, 2017

(65) Prior Publication Data

US 2018/0149647 A1   May 31, 2018

Related U.S. Application Data

(63) Continuation of application No. 14/597,999, filed on Jan. 15, 2015, now Pat. No. 9,835,623.

(60) Provisional application No. 61/927,960, filed on Jan. 15, 2014.

(51) Int. Cl.
*G01N 33/561* (2006.01)
*G01N 33/53* (2006.01)
*G01N 33/543* (2006.01)

(52) U.S. Cl.
CPC ....... *G01N 33/561* (2013.01); *G01N 33/5302* (2013.01); *G01N 33/54326* (2013.01)

(58) Field of Classification Search
CPC .......... G01N 33/561; G01N 33/54326; G01N 33/5302; G01N 27/447
See application file for complete search history.

(56) References Cited

U.S. PATENT DOCUMENTS

| | | | |
|---|---|---|---|
| 5,395,498 A | 3/1995 | Gombinsky et al. | |
| 5,736,410 A | 4/1998 | Zarling et al. | |
| 6,534,013 B1 | 3/2003 | Kennedy | |
| 6,613,581 B1 | 9/2003 | Wada et al. | |
| 8,263,022 B2 | 9/2012 | Hu | |
| 9,835,623 B2* | 12/2017 | Barry | G01N 33/561 |
| 2003/0004484 A1 | 1/2003 | Hammons et al. | |
| 2003/0012966 A1 | 1/2003 | Sung | |
| 2006/0292647 A1 | 12/2006 | Green et al. | |
| 2009/0018029 A1 | 1/2009 | Miao et al. | |
| 2012/0013554 A1 | 1/2012 | Nam et al. | |
| 2012/0032904 A1 | 2/2012 | Moon et al. | |
| 2013/0078663 A1* | 3/2013 | Herr | G01N 33/561 |
| | | | 435/28 |

FOREIGN PATENT DOCUMENTS

| | | |
|---|---|---|
| CN | 102713640 A | 10/2012 |
| CN | 103097029 A | 5/2013 |
| WO | 2010041230 A2 | 4/2010 |
| WO | 2012138882 A2 | 10/2012 |

OTHER PUBLICATIONS

Chetwynd et al. "Current Application of Capillary Electrophoresis in Nanomaterial Characterisation and Its Potential to Characterise the Protein and Small Molecule Corona", Nanomaterials 2018, 8, 99; doi:10.3390/nano8020099, pp. 1-29 (Year: 2018).*
Kaneta et al. "On-column capture of a specific protein in capillary electrophoresis using magnetic beads" Electrophoresis 2006, 27, 3218-3223.
Kaneta et al. "On-column capture of a specific protein separated by SDS-CGE using an immunological reaction on magnetic beads" Electrophoresis 2007, 28, 2262-2266.
Huang et al., "Solid-Phase purification of gene synthesis products using magnetic beads", SPIE, PO Box 10 Bellingham WA 98227-0010 USA, Jan. 1, 2008 (Jan. 1, 2008), XP0240446355.
International Search Report issued in corresponding international application No. PCT/US15/11659, dated Apr. 1, 2015.
International Preliminary Report on Patentability with Written Opinion issued in corresponding international application No. PCT/US15/11659, dated Apr. 1, 2015.
Notice of Allowance with listing of references, issued in corresponding U.S. Appl. No. 14/597,999, dated Nov. 8, 2017.

(Continued)

*Primary Examiner* — Christine Foster
(74) *Attorney, Agent, or Firm* — Valeriya Svystun; Day Pitney LLP

(57) ABSTRACT

A microfluidic Western blot method and system including a microfluidic western blot method for immunoassay of proteins, the method including introducing a sample including the proteins onto a chip; electrophoretically separating the proteins; binding the separated proteins to beads to form protein-attached beads, the beads being magnetic; flowing the protein-attached beads into a magnetic holding region; applying a magnetic field to the magnetic holding region to fix the protein-attached beads in place within the magnetic holding region; binding primary antibodies to target proteins on the protein-attached beads; binding secondary antibodies to the bound primary antibodies; and detecting the bound secondary antibodies.

5 Claims, 8 Drawing Sheets

(56) References Cited

OTHER PUBLICATIONS

SIPO's first Office Action, issued in corresponding Chinese patent application No. 2015800047674, Mar. 2018. (English language translation), 15 pages total.
European Examination Report, issued in corresponding European patent application No. 15704409.0, dated Jun. 7, 2018, 5 pages total.
European Communication issued in corresponding application No. EP 15 704 409.0, dated Nov. 6, 2019, (4 pages).

* cited by examiner

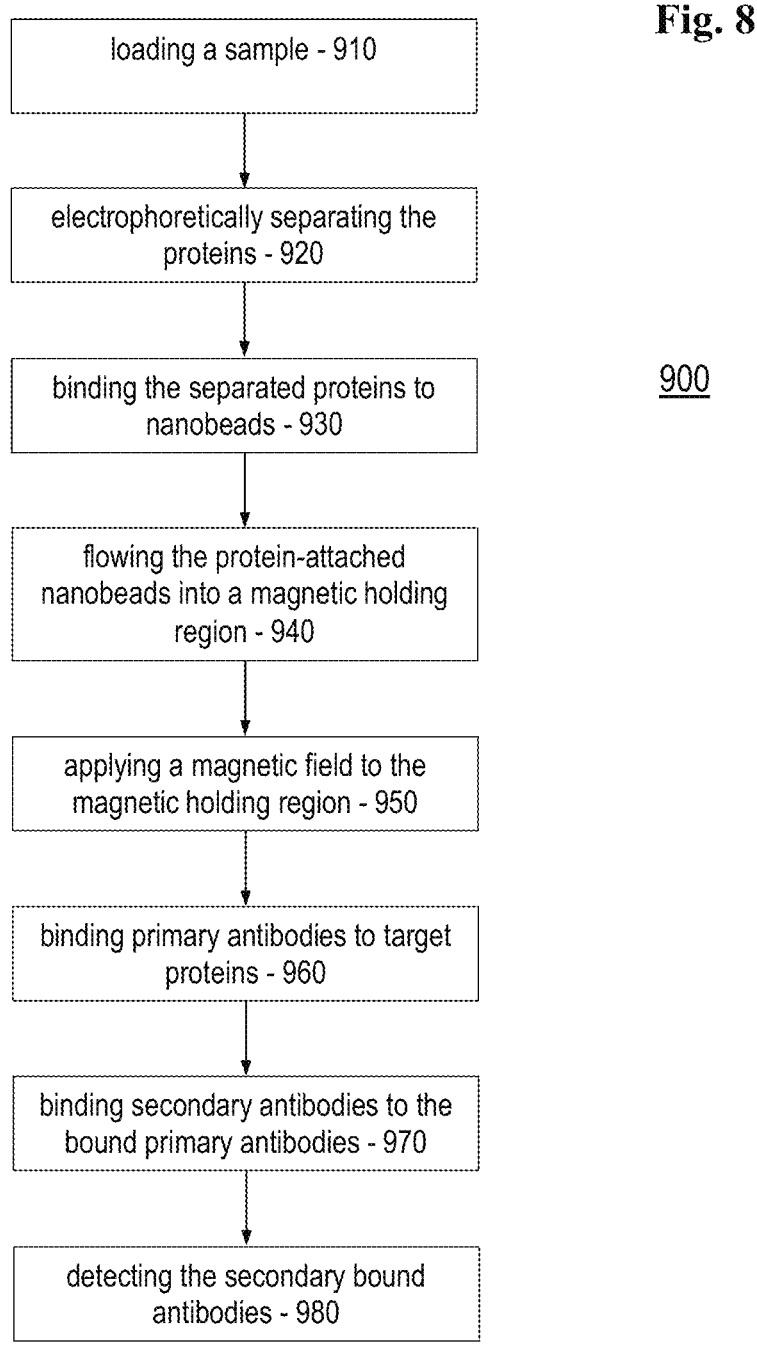

METHOD AND SYSTEM OF MICROFLUIDIC IMMUNOASSAY USING MAGNETIC BEADS

CROSS REFERENCE TO RELATED APPLICATIONS

This application is a continuation of and claims the benefit of priority to U.S. patent application Ser. No. 14/597,999, filed Jan. 15, 2015, now U.S. Pat. No. 9,835,623, which claims the benefit of priority to U.S. Provisional Patent Application Ser. No. 61/927,960, filed Jan. 15, 2014. The content of each of the aforementioned patent applications is incorporated herein by reference in its entirety for any purpose whatsoever.

TECHNICAL FIELD

The technical field of this disclosure is assay systems, particularly, methods and systems of microfluidic immunoassay using magnetic beads.

BACKGROUND OF THE INVENTION

The use of microfluidic technology has been proposed for a number of analytical chemical and biochemical operations. This technology allows one to perform chemical and biochemical reactions, macromolecular separations, and the like, that range from the simple to the relatively complex, in easily automated, high-throughput, low-volume systems. Further information about microfluidic devices and systems is presented in U.S. Pat. No. 6,534,013 to Kennedy, issued Mar. 18, 2003, and incorporated in its entirety herein by reference.

As used herein, the term "microfluidic," or the term "microscale" when used to describe a fluidic element, such as a passage, chamber or conduit, generally refers to one or more fluid passages, chambers or conduits which have at least one internal cross-sectional dimension, e.g., depth or width, of between about 0.1 µm and 500 µm. In the devices of the present invention, the microscale channels preferably have at least one cross-sectional dimension between about 0.1 µm and 200 µm, more preferably between about 0.1 µm and 100 µm, and often between about 0.1 µm and 20 µm.

In general, microfluidic systems include a microfluidic device, or chip, that has networks of integrated submicron channels in which materials are transported, mixed, separated, and detected. Microfluidic systems typically also contain components that provide fluid driving forces to the chip and that detect signals emanating from the chip.

Microfluidic chips may be fabricated from a number of different materials, including glass or polymeric materials. An example of a commercially available microfluidic chip is the DNA LabChip® manufactured by Caliper Life Sciences, Inc. of Hopkinton, Mass., and used with the Agilent 2100 Bioanalyzer system manufactured by Agilent Technologies, Inc. of Palo Alto, Calif. The chip has two major components: a working part made of glass, and a plastic caddy or mount bonded to the working part. The working part contains microfluidic channels in its interior, and wells on its exterior that provide access to the microfluidic channels. The working part is typically fabricated by bonding together two or more planar substrate layers. The microfluidic channels in the working part are formed when one planar substrate encloses grooves formed on another planar substrate. The mount protects the working part of the chip, and provides for easier handling of the chip by a user. The increased ease of handling partially results from the fact that the mount is larger than the working part of the device, which in many cases is too small and thin to be easily handled. The mount may be fabricated from any suitable polymeric material, such as an acrylic or thermoplastic. The glass working part is typically bonded to the polymeric mount using a UV-cured adhesive. Reservoirs in the mount provide access to the wells on the working part of the chip. The reservoirs hold much greater volumes of material than the wells in the working part, thus providing an interface between the macro-environment of the user and the microenvironment of the wells and channels of the microfluidic device.

This type of microfluidic chip is a "planar" chip. In a planar chip, the only access to the microchannels in the chip is through the reservoirs in the caddy and in-turn through the wells in the working part. Another type of microfluidic chip is a "sipper" chip, which has a small tube or capillary (the "sipper") extending from the chip through which fluids stored outside the chip can be directed into the microfluidic channels in the chip. Typical sipper chips have between one and twelve sippers. In use, the sipper is placed in a receptacle having sample material and minute quantities of the sample material are introduced, or "sipped" through the capillary tube to the microfluidic channels of the chip. This sipping process can be repeated to introduce any number of different sample materials into the chip. Sippers make it easier to carry out high-throughput analysis of numerous samples on a single microfluidic chip.

Western blot electrophoresis assays have been developed to detect specific proteins in a sample. The process can be divided into three parts: protein separation, sample transfer, and immunoassay. In protein separation, mechanical and/or chemical techniques are applied to a sample, such as a tissue sample, to expose proteins. The proteins are then separated with gel electrophoresis in which the speed of movement of the different proteins through the gel under a differential voltage is governed by the molecular weight of the individual proteins. In sample transfer, the separated proteins are moved from within the gel onto a membrane in a process called electroblotting, which uses electric current to move the proteins. In immunoassay, a primary antibody is attached to target proteins on the membrane, a secondary antibody is attached to the primary antibody, and a light emitter reacts with the secondary antibody to produce light at each of the target proteins. Detection of the light provides identification and quantification of the target proteins.

Although the current method of Western blot electrophoresis assay provides valuable results, the current method has a number of problems. The current method is a labor-intensive process, performed manually and requiring gel plates and special membrane paper to transfer the separated proteins. The manual nature of the process increases the cost and limits the number of samples which can be tested. A typical Western analysis requires between 8 and 24 hours of monitored operation, with almost half requiring hands-on, manual operation.

It would be desirable to have methods and systems of microfluidic immunoassay using magnetic beads that would overcome the above disadvantages.

SUMMARY OF THE INVENTION

One aspect of the invention provides a microfluidic Western blot method for immunoassay of proteins, the method including introducing a sample including the proteins onto a chip; electrophoretically separating the proteins; binding the separated proteins to beads to form protein-attached beads, the beads being magnetic; flowing the protein-attached beads into a magnetic holding region; applying a magnetic field to the magnetic holding region to fix the protein-attached beads in place within the magnetic holding region; binding primary antibodies to target proteins on the protein-attached beads; binding secondary antibodies to the bound primary antibodies; and detecting the bound secondary antibodies.

Another aspect of the invention provides a microfluidic western blot method for immunoassay of proteins, the method including providing a microfluidic chip having a substrate defining a sample well, a separation region operably coupled to the sample well, and a magnetic holding region operably coupled to the separation region; introducing a sample including the proteins into the sample well; flowing the sample into the separation region; applying a voltage across the separation region to electrophoretically separate the proteins in the separation region; binding the electrophoretically separated proteins to beads to form protein-attached beads, the beads being magnetic; flowing the protein-attached beads into the magnetic holding region; applying a magnetic field to the magnetic holding region to fix the protein-attached beads in place within the magnetic holding region; binding primary antibodies to target proteins on the protein-attached beads; binding secondary antibodies to the bound primary antibodies; and detecting the bound secondary antibodies.

Another aspect of the invention provides a microfluidic Western blot system for immunoassay of proteins with beads, the system including a microfluidic chip having a substrate defining a sample well, a separation region operably coupled to the sample well, and a magnetic holding region operably coupled to the separation region; and an electromagnet operably connected to provide a magnetic field to the magnetic holding region, the magnetic field being operable to fix the beads in place within the magnetic holding region.

Another aspect of the invention provides a microfluidic method for immunoassay of analytes, the method including resolving in a first fluid region one or more analytes in a sample disposed within the first fluid region based on size and charge of the one or more analytes; binding the resolved analytes to magnetic beads to form analyte-attached beads; applying a magnetic field to fix at least a portion of the analyte-attached beads in place; binding a detection reagent to the analyte-attached beads; and detecting the detection reagent.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIG. 8 is a flow chart of a microfluidic Western blot method in accordance with the invention.

Like elements share like reference numbers between and among the various figures.

DETAILED DESCRIPTION

Figure 1:
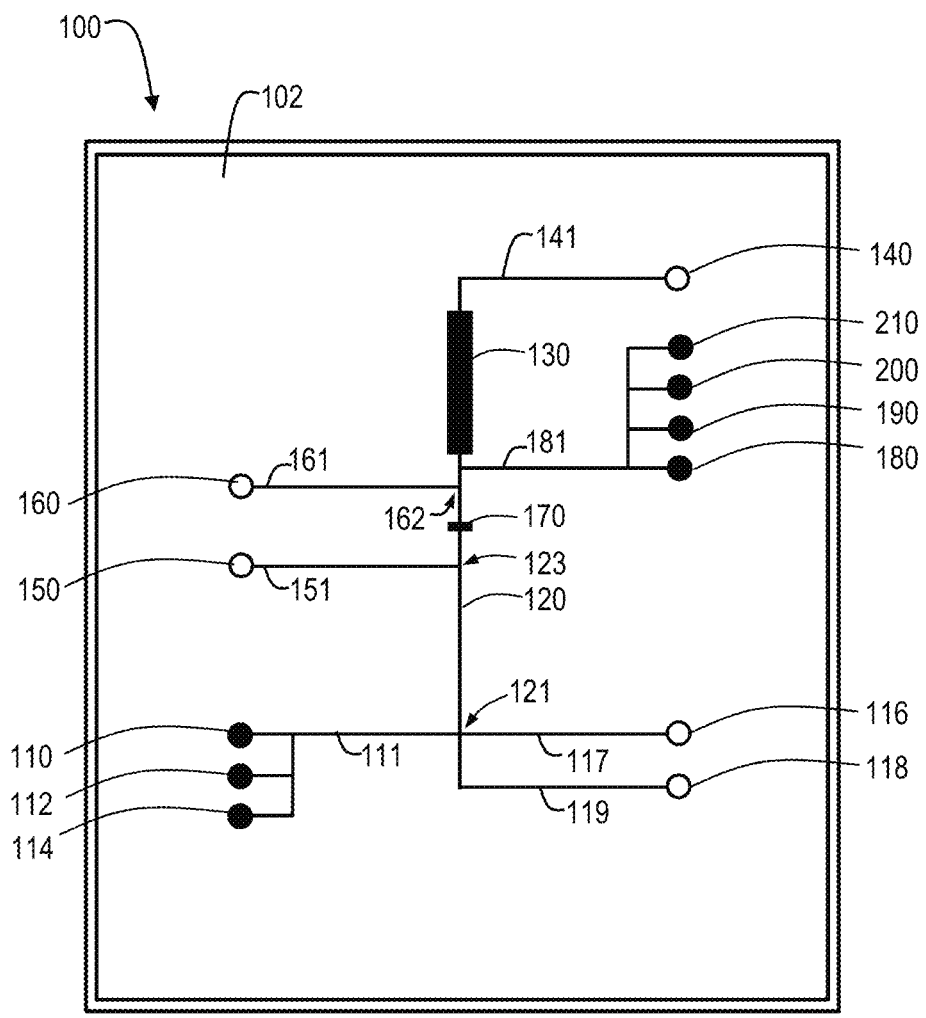
FIG. 1 is a schematic top view of one embodiment of a microfluidic Western blot device with multiple sample wells, separate destain and beads wells, and a detection reagent well made in accordance with the invention.

FIG. 1 is a schematic top view of one embodiment of a microfluidic Western blot device with multiple sample wells, separate destain and beads wells, and a detection reagent well made in accordance with the invention.

The microfluidic chip 100 has a substrate 102 which defines a number of wells and channels for performing a Western blot method of immunoassay. In this embodiment, the substrate 102 defines a sample well 110, a separation region 120 operably coupled to the sample well 110, and a magnetic holding region 130 operably coupled to the separation region 120.

The sample well 110 can be connected to the separation region 120 by a sample channel 111. The sample well 110 can also be operably connected to an injection electrode 116 through an injection channel 117 through the sample channel 111. In operation, the sample including the proteins can be flowed from the sample well 110 through the sample channel 111 into the injection channel 117 by applying a differential voltage between the sample well 110 and the injection electrode 116. The injection channel 117 can be operably connected to the first separation electrode channel 119. The sample can be flowed from the injection channel 117 to the first separation electrode channel 119 by applying a differential voltage between the injection electrode 116 and first separation electrode 118 operably connected to the first separation electrode channel 119. In one embodiment, the differential voltage used to move the proteins around the chip can be a high differential voltage, in contrast with a low differential voltage which can be used to move immunoassay chemicals through the magnetic holding region.

In this example, the microfluidic chip 100 includes a number of sample wells 110, 112, 114. The samples from the sample wells can be processed sequentially, i.e., the sample from sample well 110 can be processed first, followed by the sample from the sample well 112 and the sample well 114. Those skilled in the art will appreciate that the microfluidic chip 100 can include any number of sample wells as desired for a particular application.

The first separation electrode channel 119 can be operably connected to the separation region 120. The separation region 120 is primed with gel and dye so that electrophoresis can be performed on the sample in the separation region 120.

The separation region 120 can also be connected to a second separation electrode 140 through the magnetic holding region 130 and second separation electrode channel 141.

Electrophoresis can be performed on the sample by applying a differential voltage between the first separation electrode 118 and the second separation electrode 140. Electrophoresis separates the proteins in the sample into one or more protein peaks as the lower molecular weight proteins move more quickly than the heavier molecular weight proteins move more quickly than the heavier molecular weight proteins through the gel of the separation region 120 between the upstream end 121 and the downstream end 123. The differential voltage between the first separation electrode 118 and the second separation electrode 140 can also be used to move the sample from the separation region 120 to the magnetic holding region 130.

A destain well 150 can be operably connected to the downstream end 123 of the separation region 120 through a destain channel 151 to add destaining solution to the separated sample leaving the separation region 120. The destaining solution removes detergent (SDS) micelles to allow visualization of protein peaks in the sample and reduce signal background. The destaining solution can be flowed into the sample by applying a differential voltage between an electrode associated with the destain well 150 and the second separation electrode 140.

A peak detection region 170 can be provided between the separation region 120 and the magnetic holding region 130. A peak optical detector (not shown) monitoring the peak detection region 170 can detect the protein peaks in the sample moving through the peak detection region 170, which can be used to detect when the last protein peak enters the magnetic holding region 130.

A bead well 160 can be operably connected to the downstream end 162 of the peak detection region 170 through a bead channel 161 to add beads to the separated sample leaving the peak detection region 170. The surfaces of the beads are functionalized to attach to any and all proteins in the sample to form protein-attached beads. Further, the beads are magnetic and can be magnetically manipulated within the magnetic holding region 130. In one embodiment, the beads can be primary antibody attached beads, i.e., a bead with a primary antibody attached to the bead at the time of manufacture and before the bead is introduced onto the chip. Exemplary beads are available from PerkinElmer chemagen Technologie GmbH Baesweiler, Germany. In one embodiment, the beads can be nanobeads. The beads can be flowed into the sample by applying a differential voltage between an electrode associated with the bead well 160 and the second separation electrode 140.

An immunoassay channel 181 can be attached downstream of the bead channel 161 and before the magnetic holding region 130 to allow addition of immunoassay chemicals. In this example, the immunoassay channel 181 is operably connected to a blocking buffer well 180, a primary antibody well 190, a secondary antibody well 200, and a detection reagent well 210. When differential voltage between the first separation electrode 118 and the second separation electrode 140 is used to move the sample into the magnetic holding region 130, the differential voltage can be turned off before the immunoassay chemicals are added.

In operation, when the last protein peak enters the magnetic holding region 130, the differential voltage between the first separation electrode 118 and the second separation electrode 140 can be turned off and an electromagnet (not shown) operably connected to the magnetic holding region 130 can be energized to fix the protein-attached beads in place within the magnetic holding region 130. In one example, the magnetic field is generated by a circular electromagnet maintaining the protein-attached beads dispersed across the capillary section within the magnetic holding region 130.

The immunoassay chemicals from each of the blocking buffer well 180, primary antibody well 190, secondary antibody well 200, and detection reagent well 210 can be flowed through the magnetic holding region 130 to contact the protein-attached beads in turn by applying a differential voltage between an electrode associated with each of the wells and the second separation electrode 140. The magnetic holding region 130 can be washed between application of each of the immunoassay chemicals as desired for a particular application by applying a differential voltage between an electrode associated with the destain well 150 and the second separation electrode 140. Each of the immunoassay chemicals can be allowed to incubate within the magnetic holding region 130 to provide a desired incubation time and/or temperature as desired for a particular application by removing the differential voltage between the electrode associated with each of the wells and the second separation electrode 140 after one of the immunoassay chemicals has been flowed into the magnetic holding region 130.

A blocking buffer can be flowed into the magnetic holding region 130 by applying a differential voltage between an electrode associated with the blocking buffer well 180 and the second separation electrode 140. The blocking buffer is used after protein binding to the beads to saturate all remaining protein binding sites of the beads and prevent non-specific immunoassay reagents binding to the beads. Those skilled in the art will appreciate that the immunoassay can be performed without use of a blocking buffer as desired for a particular application. Any unbound blocking buffer can be washed from the magnetic holding region 130 by applying a differential voltage between the electrode associated with the destain well 150 and the second separation electrode 140.

A primary antibody can be flowed into the magnetic holding region 130 by applying a differential voltage between an electrode associated with the primary antibody well 190 and the second separation electrode 140. The primary antibody binds with target proteins on the protein-attached beads. Any unbound primary antibody can be washed from the magnetic holding region 130 by applying a differential voltage between the electrode associated with the destain well 150 and the second separation electrode 140. In one example, the microfluidic chip 100 includes a heating element (not shown) operably connected to the magnetic holding region 130 to incubate the primary antibody on the protein-attached beads at a temperature as desired for a particular application.

A secondary antibody can be flowed into the magnetic holding region 130 by applying a differential voltage between an electrode associated with the secondary antibody well 200 and the second separation electrode 140. The secondary antibody binds with the primary antibody bound to the protein-attached beads. Any unbound secondary antibody can be washed from the magnetic holding region 130 by applying a differential voltage between the electrode associated with the destain well 150 and the second separation electrode 140.

A detection reagent can be flowed into the magnetic holding region 130 by applying a differential voltage between an electrode associated with the detection reagent well 210 and the second separation electrode 140. The detection reagent reacts with the secondary antibody bound to the primary antibody, which is bound to the target protein. In one example, the secondary antibody includes a coupled enzyme (such as horseradish peroxidase HRP, for example) and the detection reagent is an enzyme substrate (such as horseradish peroxidase tyramide signal amplification HRP/TSA, for example) which reacts with the coupled enzyme and generates light.

An immunoassay optical detector (not shown) can be used to detect light from the secondary antibodies. In one embodiment, the immunoassay optical detector is operably connected to receive light from the magnetic holding region 130 when the protein-attached beads are fixed in place within the magnetic holding region 130. The magnetic field in the magnetic holding region 130 can be released after the light is measured and the sample can be removed from the microfluidic chip 100. In another embodiment, the immunoassay optical detector is operably connected to receive light from the protein-attached beads as the protein-attached beads flow past the immunoassay optical detector within the magnetic field in the magnetic holding region 130 has been released and a differential voltage has been applied between the first separation the electrode 118 and the second separation electrode 140.

A waste well can be associated with the second separation electrode 140 so that the sample can be removed from the microfluidic chip 100 by application of a differential voltage between the first separation the electrode 118 and the second separation electrode 140. In one embodiment, another sample, such as a sample from the second sample well 112, can be tested after the first sample is removed from the chip. In another embodiment, another sample, such as a sample from the second sample well 112, can be moved into the separation region 120 at the same time that the first sample is being removed from the chip.

Those skilled in the art will appreciate that the microfluidic chip 100 can be adapted as desired for a particular application. In one embodiment, one or more of the separation region 120, the peak detection region 170, and/or the magnetic holding region 130 is a channel. In another embodiment, one or more of the separation region 120, the peak detection region 170, and/or the magnetic holding region 130 is a chamber. The driving force moving the sample through the microfluidic chip 100 can be differential voltage and/or differential pressure along the channels. The microfluidic chip 100 can be adapted for use in performing other types of immunoassays.

The immunoassay chemicals can also be selected as desired for a particular application. In one embodiment, the primary antibody binds with a single target protein and the immunoassay optical detector receives light at a single wavelength to identify and quantify the single target protein. In another embodiment, multiplexing can be performed on a single chip, where the primary antibody is a mixture of antibodies that bind with different target proteins and are associated with different secondary antibodies. The difference secondary antibodies can generate light at different wavelengths, so that more than one target protein can be identified and quantified at one time when receiving light from the magnetic holding region at the immunoassay optical detector.

FIGS. 2-7 illustrate various combinations of the elements of different microfluidic Western blot devices. Those skilled in the art will appreciate that the various elements can be provided in different combinations as desired for a particular application.

Figure 2:
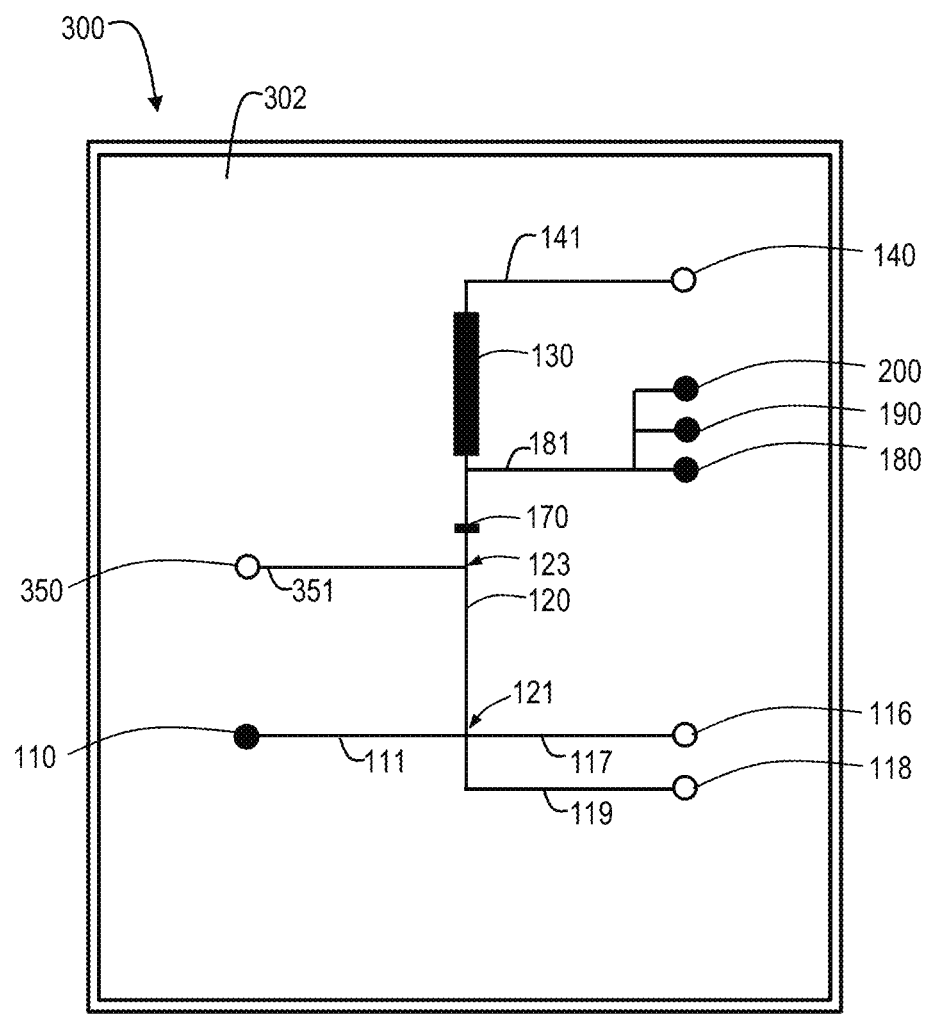
FIG. 2 is a schematic top view of one embodiment of a microfluidic Western blot device with a combined destain and bead well made in accordance with the invention.

FIG. 2 is a schematic top view of one embodiment of a microfluidic Western blot device with a combined destain and bead well made in accordance with the invention. In this embodiment, the microfluidic chip 300 has a substrate 302 which forms a destain/bead well 350 operably connected to the downstream end 123 of the separation region 120 through a destain/bead channel 351 to add a mixture of the destaining solution and beads to the separated sample leaving the separation region 120. The mixture of destaining solution and beads can be used to wash the immunoassay chemicals (blocking buffer, primary antibodies, secondary antibodies) from the magnetic holding region. This embodiment includes a single sample well 110 rather than multiple sample well and omits the detection reagent well connected to the immunoassay channel 181.

Figure 3:
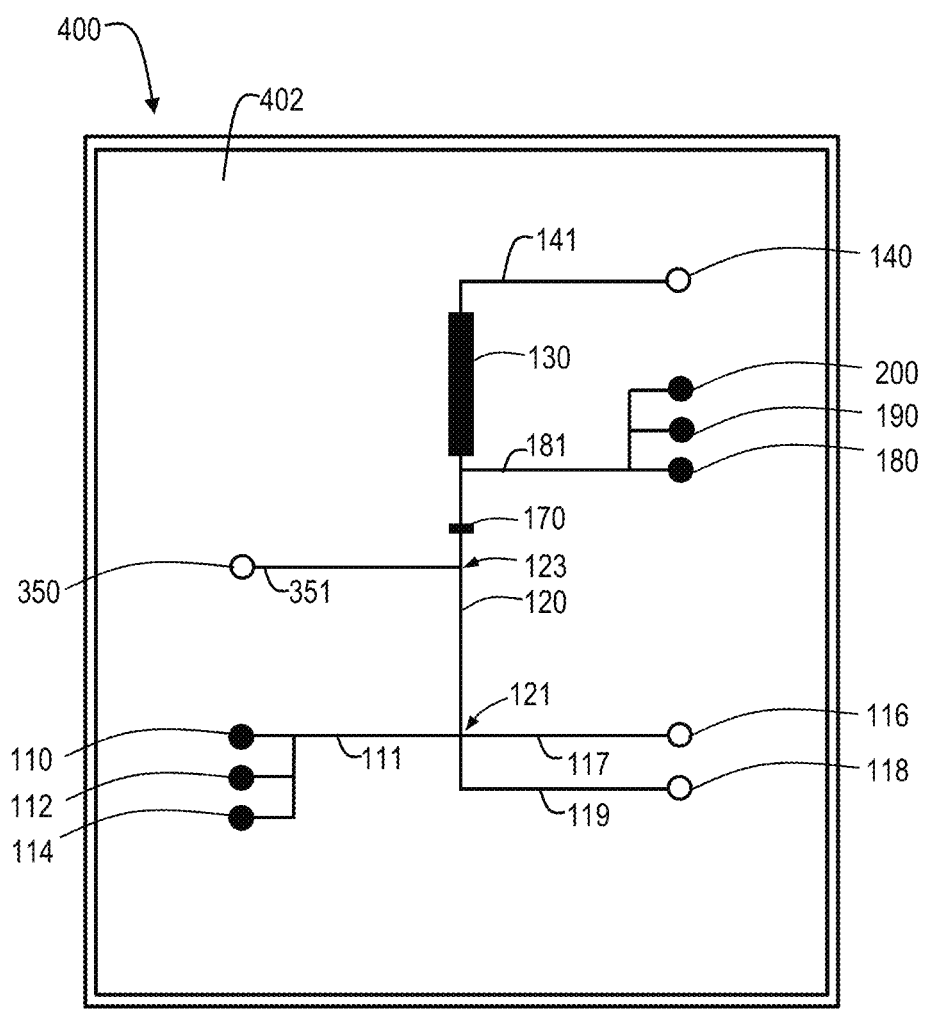
FIG. 3 is a schematic top view of one embodiment of a microfluidic Western blot device with multiple sample wells and a combined destain and bead well made in accordance with the invention.

FIG. 3 is a schematic top view of one embodiment of a microfluidic Western blot device with multiple sample wells and a combined destain and bead well made in accordance with the invention. In this embodiment, the microfluidic chip 400 has a substrate 402 which forms a destain/bead well 350 operably connected to the downstream end 123 of the separation region 120 through a destain/bead channel 351 to add a mixture of the destaining solution and beads to the separated sample leaving the separation region 120. This embodiment includes a multiple sample wells 110, 112, 114 and omits the detection reagent well connected to the immunoassay channel 181.

Figure 4:
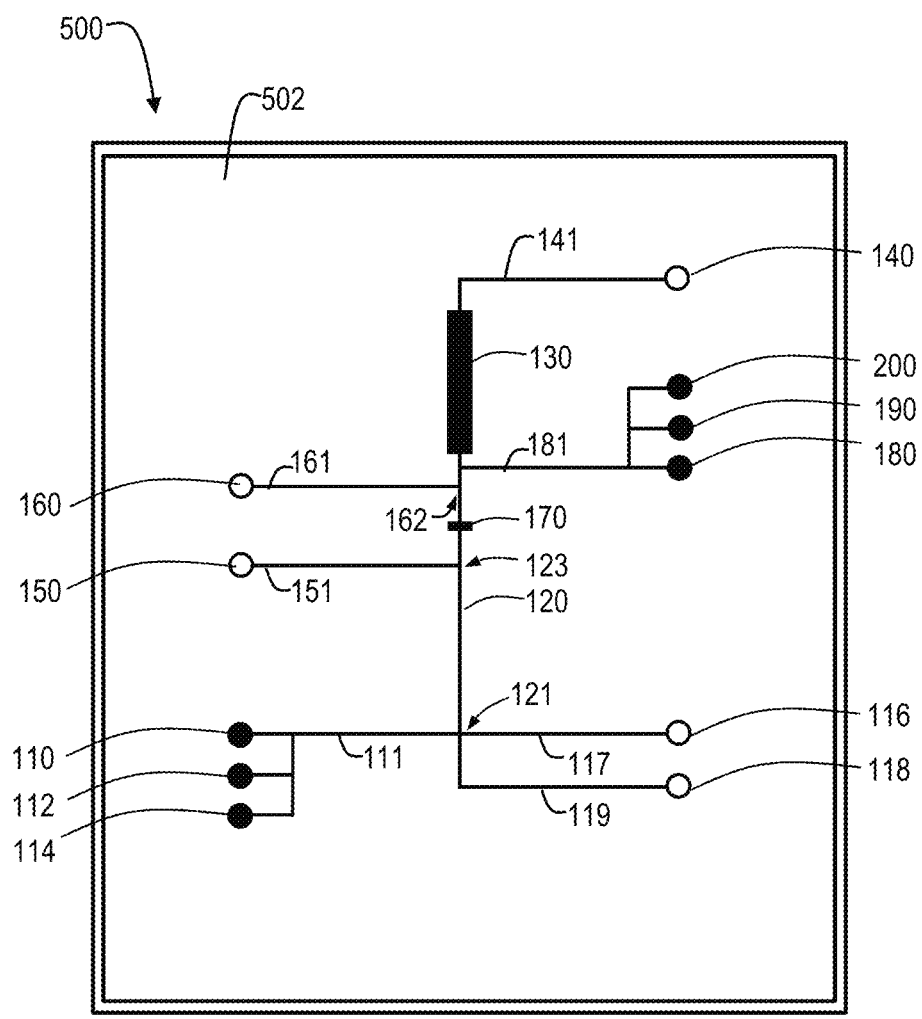
FIG. 4 is a schematic top view of one embodiment of a microfluidic Western blot device with multiple sample wells and separate destain and bead wells made in accordance with the invention.

FIG. 4 is a schematic top view of one embodiment of a microfluidic Western blot device with multiple sample wells and separate destain and bead wells made in accordance with the invention. In this embodiment, the microfluidic chip 500 has a substrate 502 which forms multiple sample wells 110, 112, 114. This embodiment includes a separate destain well 150 and bead well 160, to avoid bead in the peak detection region 170 and beads in the destaining solution used to wash the immunoassay chemicals (blocking buffer, primary antibodies, secondary antibodies) from the magnetic holding region. This embodiment also omits the detection reagent well connected to the immunoassay channel 181.

Figure 5:
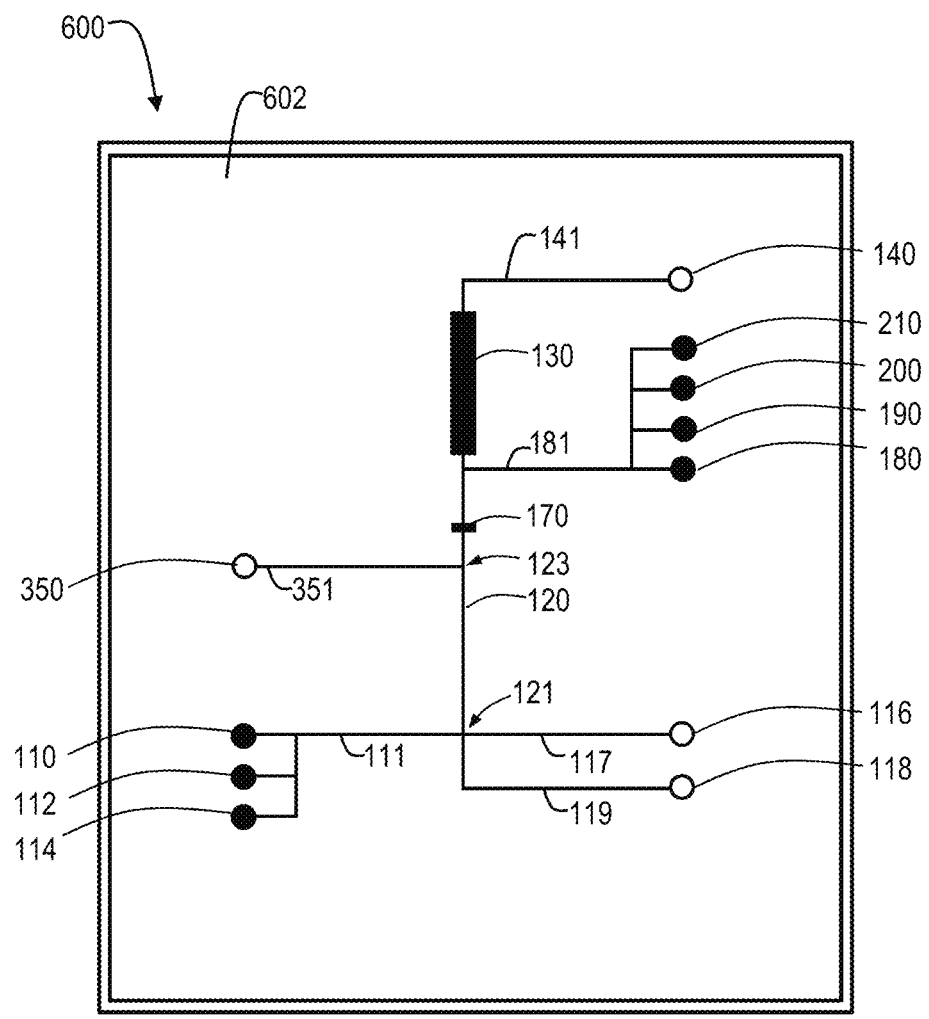
FIG. 5 is a schematic top view of one embodiment of a microfluidic Western blot device with multiple sample wells, a combined destain and bead well, and a detection reagent well made in accordance with the invention.

FIG. 5 is a schematic top view of one embodiment of a microfluidic Western blot device with multiple sample wells, a combined destain and bead well, and a detection reagent well made in accordance with the invention. In this embodiment, the microfluidic chip 600 has a substrate 602 which form multiple sample wells 110, 112, 114. This embodiment includes a destain/bead well 350 operably connected to the downstream end 123 of the separation region 120 through a destain/bead channel 351 to add a mixture of the destaining solution and beads to the separated sample leaving the separation region 120. This embodiment also includes the detection reagent well 210 operably connected to the immunoassay channel 181.

Figure 6:
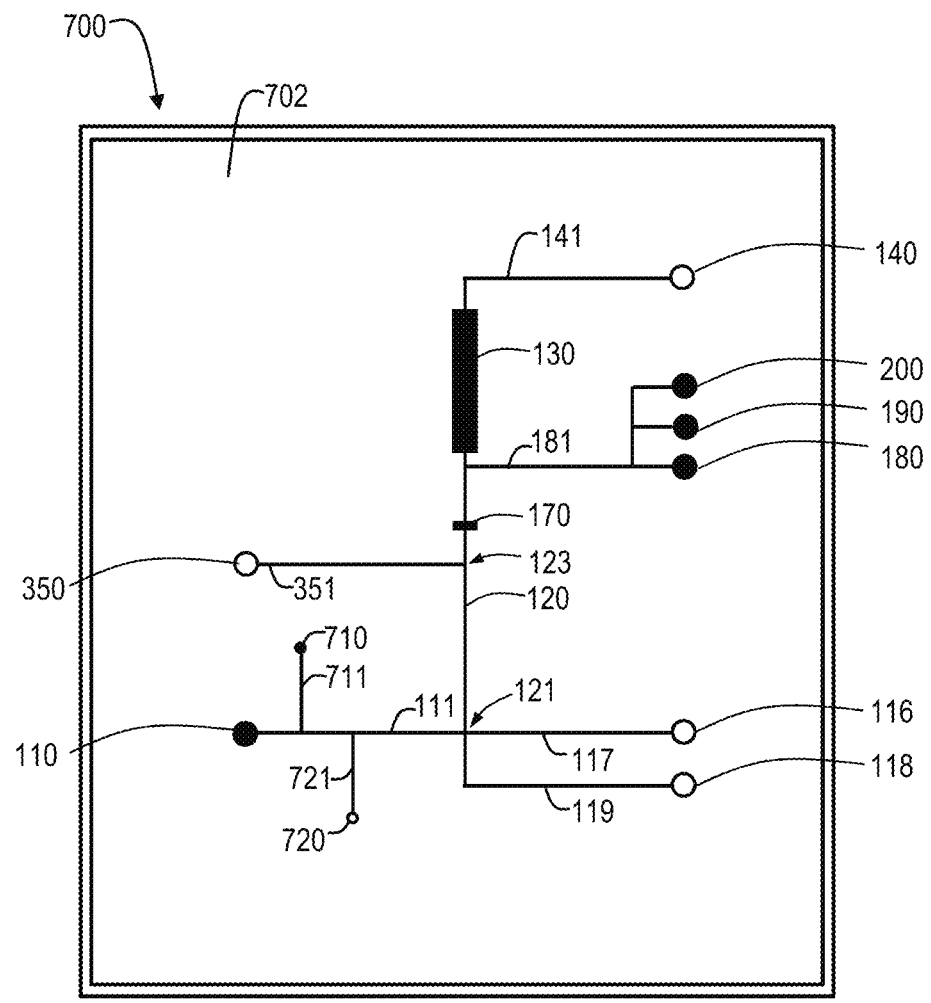
FIG. 6 is a schematic top view of one embodiment of a microfluidic Western blot device with a sample sipper made in accordance with the invention.

FIG. 6 is a schematic top view of one embodiment of a microfluidic Western blot device with a sample sipper made in accordance with the invention. In this embodiment, the microfluidic chip 700 has a substrate 702 which forms a low-pressure port 710 operably connected to the sample channel 111 by a low-pressure port channel 711 and a sipper port 720 operably connected to the sample channel 111 by a sipper port channel 721. In operation, the low-pressure port 710 is held at a lower pressure than the sipper port 720, which has been introduced into a sample well of a well plate (not shown), such as a 96-well plate or the like. The sample contained in the well plate is drawn into the sample channel 111 through the sipper port 720. In this example, multiple samples from the well plate can be processed through the microfluidic chip 700 using the same immunoassay chemicals from the blocking buffer well 180, the primary antibody well 190, and the secondary antibody well 200.

Figure 7:
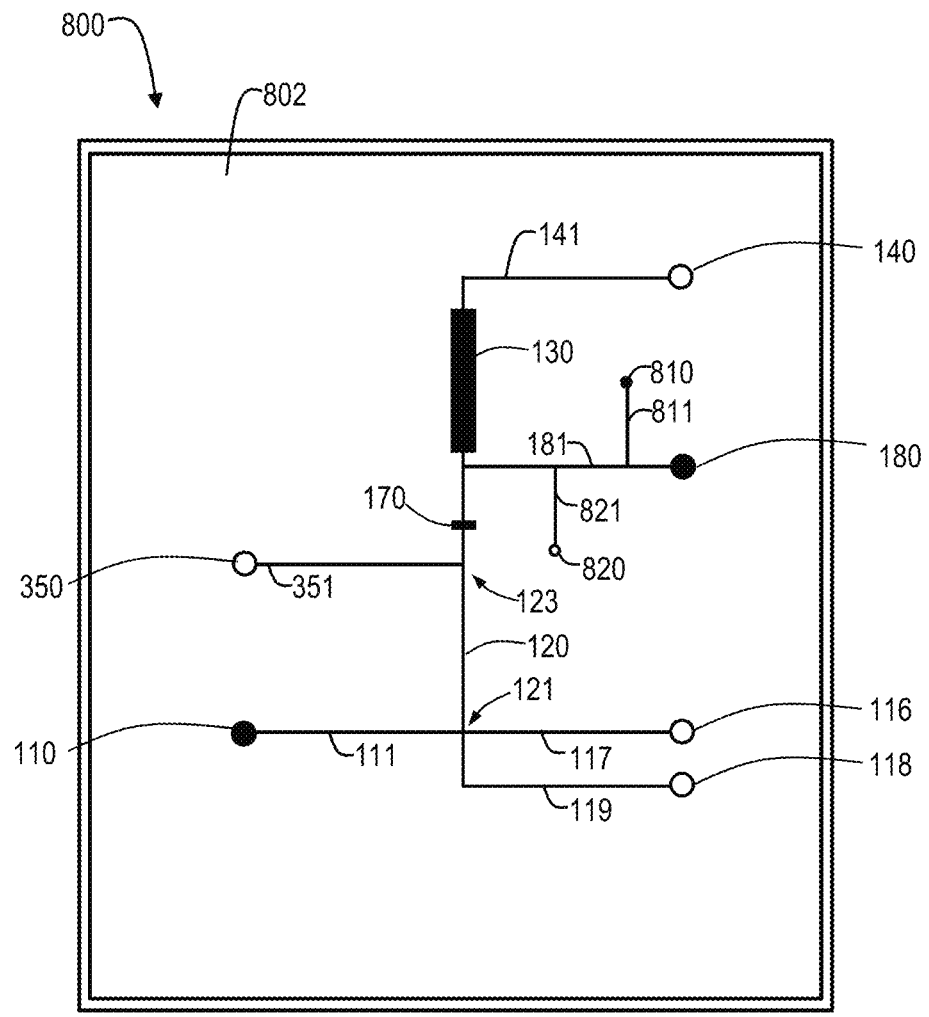
FIG. 7 is a schematic top view of one embodiment of a microfluidic Western blot device with an antibody sipper made in accordance with the invention.

FIG. 7 is a schematic top view of one embodiment of a microfluidic Western blot device with an antibody sipper made in accordance with the invention. In this embodiment, the microfluidic chip 800 has a substrate 802 which forms a low-pressure port 810 operably connected to the immunoassay channel 181 by a low-pressure port channel 811 and a sipper port 820 operably connected to the immunoassay channel 181 by a sipper port channel 821. In operation, the low-pressure port 810 is held at a lower pressure than the sipper port 820, which has been introduced into an antibody well of a well plate (not shown), such as a 96-well plate or the like. The antibody contained in the well plate is drawn into the immunoassay channel 181 through the sipper port 820. In this example, multiple antibodies from the well plate can be processed through the microfluidic chip 800 using the same sample from the sample well 110.

FIG. 8 is a flow chart of a microfluidic Western blot method in accordance with the invention. The microfluidic Western blot method 900 for immunoassay of proteins includes introducing a sample 910 including the proteins onto a chip; electrophoretically separating the proteins 920; binding the separated proteins to beads 930 to form protein-attached beads, the beads being magnetic; flowing the protein-attached beads into a magnetic holding region 940; applying a magnetic field to the magnetic holding region 950 to fix the protein-attached beads in place within the magnetic holding region; binding primary antibodies to target proteins 960 on the protein-attached beads; binding secondary antibodies to the bound primary antibodies 970; and detecting the bound secondary antibodies 980. The method 900 can be performed using a microfluidic chip having a substrate defining a sample well, an separation region operably coupled to the sample well, and a magnetic holding region operably coupled to the separation region, as illustrated in FIGS. 1-7.

Referring to FIG. 8, introducing a sample 910 including the proteins onto a chip moves the sample into position to perform the Western blot method. In one embodiment, the sample can be loaded by applying a differential voltage between electrodes on the chip. In another embodiment, the sample can be loaded by applying a differential pressure between ports on the chip. Those skilled in the art will appreciate that the sample can be loaded in any way desired for a particular application. In one embodiment, the method 900 can include priming the chip with gel and dye before the introducing 910.

Electrophoretically separating the proteins 920 can include applying a differential voltage to separate the proteins in the sample into one or more protein peaks as the lower molecular weight proteins move more quickly than the heavier molecular weight proteins through the gel of a separation region on the chip.

Binding the separated proteins to beads 930 to form protein-attached beads attaches substantially all of the separated proteins in the sample to the beads. The beads are magnetic, so the protein-attached beads can be moved by a magnetic field. In one embodiment, the binding the separated proteins to beads 930 can include destaining the proteins before binding the separated proteins to the beads. The electrophoretically separating the proteins 920 can then further include detecting migrating peaks in the destained proteins. The flowing the protein-attached beads into a magnetic holding region 940 can then further include flowing the protein-attached beads into the magnetic holding region until a last one of the migrating peaks is detected at which point all of the protein-attached beads will be in the magnetic holding region.

Flowing the protein-attached beads into a magnetic holding region 940 places the protein-attached beads in position in the magnetic holding region for immunoassay. In one embodiment, the protein-attached beads can flow from applying a differential voltage between electrodes on the chip. In another embodiment, the protein-attached beads can flow from applying a differential pressure between ports on the chip. Those skilled in the art will appreciate that the protein-attached beads can be made to flow into a magnetic holding region in any way desired for a particular application.

Applying a magnetic field to the magnetic holding region 950 to fix the protein-attached beads in place within the magnetic holding region holds the protein-attached beads in place during the immunoassay. In one example, the magnetic field from an electromagnet can hold the protein-attached beads to the base of the magnetic holding region. The magnetic field also can preserve the relative position of the protein peaks of the sample within the magnetic holding region.

Binding primary antibodies to target proteins 960 on the protein-attached beads tags the target proteins for detection while leaving proteins which are not of interest untagged. In one embodiment, the binding primary antibodies to target proteins 960 can include incubating the primary antibodies on the protein-attached beads and washing unbound primary antibodies from the magnetic holding region. In another embodiment, the method 900 can include flowing blocking buffer through the magnetic holding region over the protein-attached beads before the binding primary antibodies. The method 900 can then further include incubating the blocking buffer on the protein-attached beads and washing unbound blocking buffer from the magnetic holding region.

Binding secondary antibodies to the bound primary antibodies 970 tags the bound primary antibodies with the secondary antibodies to be used in identifying the bound primary antibodies, which are attached to the target proteins. In one embodiment, the binding secondary antibodies to the bound primary antibodies 970 can include washing unbound secondary antibodies from the magnetic holding region.

Detecting the bound secondary antibodies 980 can provide an indication of the target proteins in the sample, since the bound secondary antibodies are attached to the bound primary antibodies, which are attached to the target proteins. In one embodiment, the method 900 includes flowing detection reagent through the magnetic holding region over the protein-attached beads before the detecting 980 and the detecting the bound secondary antibodies 980 includes detecting light emitted from reaction of the detection reagent with the bound secondary antibodies.

The detecting the bound secondary antibodies 980 can be performed with the sample in the magnetic holding region or as the sample flows from the magnetic holding region. In one embodiment, the detecting 980 can include detecting the bound secondary antibodies in the magnetic holding region with the magnetic field applied to the magnetic holding region. In another embodiment, the method 900 can include releasing the magnetic field in the magnetic holding region to release the protein-attached beads. The detecting 980 can then include detecting the bound secondary antibodies flowing by a stationary detector.

The method 900 can continue with emptying the magnetic holding region and/or introducing a new sample for analysis. In one embodiment, the method 900 can include releasing the magnetic field in the magnetic holding region to release the protein-attached beads. The method 900 can further include introducing a second sample onto the chip and performing a Western blot analysis on the second sample as desired. In one embodiment, the second sample can be tested after the first sample is removed from the chip. In another embodiment, the second sample can be electrophoretically separated at the same time that the first sample is being removed from the chip. Washes of the chip can be provided between sequential samples to prevent cross contamination as desired for a particular application.

It is important to note that FIGS. 1-8 illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention. The examples above deal primarily with Western blot immunoassay of proteins on a chip using magnetic nanobeads, but those skilled in the art will appreciate that the method and system of microfluidic immunoassay using magnetic beads can be applied equally well to immunoassay of any analytes on a chip using magnetic beads.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A microfluidic method for immunoassay of analytes, the method comprising:

electrophoretically separating one or more analytes in a sample disposed within a first fluid region of a microfluidic chip based on size and charge of the one or more analytes;

binding the one or more electrophoretically separated analytes to magnetic beads to form analyte-attached beads in the first fluid region of the microfluidic chip;

flowing the analyte-attached beads into a second fluid region of the microfluidic chip prior to applying a magnetic field, wherein the second fluid region comprises a magnetic holding region;

applying the magnetic field to fix at least a portion of the analyte-attached beads in place within the second fluid region of the microfluidic chip;

binding a detection reagent to the analyte-attached beads within the second fluid region of the microfluidic chip; and detecting the detection reagent within the second fluid region of the microfluidic chip.

2. The method of claim 1 wherein the one or more analytes comprise proteins.

3. The method of claim 1 further comprising introducing the sample including the one or more analytes into the first fluid region.

4. The method of claim 1 wherein:

the binding the detection reagent further comprises binding primary antibodies to the analyte-attached beads; and binding secondary bodies to the bound primary antibodies; and the detecting the detection reagent further comprises detecting the bound secondary antibodies.

5. The method of claim 1 wherein:

the beads comprise primary antibody attached beads; and the binding the detection reagent further comprises binding secondary antibodies to the primary antibody attached beads.

\* \* \* \* \*